(12) United States Patent
Kaldor et al.

(10) Patent No.: US 9,902,694 B2
(45) Date of Patent: Feb. 27, 2018

(54) CRYSTALLINE FORMS

(71) Applicant: GLAXOSMITHKLINE INTELLECTUAL PROPERTY (No.2) LIMITED, Middlesex (GB)

(72) Inventors: Istvan Kaldor, Research Triangle Park, NC (US); Dalin Tang, Shanghai (CN)

(73) Assignee: GlaxoSmithKline Intellectual Property (No 2) Limited, Brentford, Middlesex (GB)

( * ) Notice: Subject to any disclaimer, the term of this patent is extended or adjusted under 35 U.S.C. 154(b) by 0 days.

(21) Appl. No.: 15/111,068

(22) PCT Filed: Jan. 20, 2015

(86) PCT No.: PCT/IB2015/050440
§ 371 (c)(1),
(2) Date: Jul. 12, 2016

(87) PCT Pub. No.: WO2015/110958
PCT Pub. Date: Jul. 30, 2015

(65) Prior Publication Data
US 2016/0332967 A1 Nov. 17, 2016

Related U.S. Application Data

(60) Provisional application No. 61/929,814, filed on Jan. 21, 2014.

(51) Int. Cl.
*A61K 31/404* (2006.01)
*C07D 209/08* (2006.01)
*C07D 209/42* (2006.01)

(52) U.S. Cl.
CPC ........ *C07D 209/42* (2013.01); *C07B 2200/13* (2013.01)

(58) Field of Classification Search
CPC .............................. A61K 31/404; C07D 209/08
USPC .......................................... 514/415; 548/503
See application file for complete search history.

(56) References Cited

U.S. PATENT DOCUMENTS 6,576,265 B1   6/2003   Spievack
8,957,104 B2 * 2/2015  Turnbull .............. C07D 209/08
                                                      514/415

FOREIGN PATENT DOCUMENTS

WO    WO 2008/042571 A2    4/2008
WO    WO 2010/118287 A1   10/2010
WO    WO 2012/097744 A1    7/2012
WO    WO 2014/013309 A1    1/2014

OTHER PUBLICATIONS

Albaaj, et al., *Postgrad. Med. J.*, 82:693-6 (2006).
Asthana, et al., *J. Ger., Series A: Biol. Sci. Med. Sci.*, 59:461-465 (2004).
Bhasin, *J. Gerontol. A Biol. Sci. Med. Sci.*, 58:1002-8 (2003).
Caminti, et al., *J. Am. Coll. Cardiology*, 54(10):919-927 (2009).
Ferrando, et al., *Am. J. Phys. Endo. Met.*, 282:E601-E-607 (2002).
Hedstrom, et al., *J. Bone Joint Surg Br.*, 84(4):497-503 (2002).
Ho, et al., *Curr. Opin. Obstet. Gynecol.*, 16:405-409 (2004).
Iellamo, et al., *J. Am. Coll. Cardiol.*, 56(16):1310-1316 (2010).
Mammadov, et al., *Int. Urol. Nephrol.*, 43:1003-1008 (2011).
Mohler, et al., *J. Med. Chem.*, 52(12):3597-617 (2009).
*Nature Biotechnology*, 26(11):1261-1268 (2008).
Smith, *Endoc. Rev.*, 2545-2571 (2004).
Svartberg, *Curr. Opin. Endocrinol Diabetes Obes.*, 17(3):257-261 (2010).
Turner, et al., *Cell and Tissue Res.*, 347(3):759-774 (2012).
Zilbermint, et al., *Future Oncology*, 5(8):1211-1220 (2009).

* cited by examiner

*Primary Examiner* — Brenda Coleman
(74) *Attorney, Agent, or Firm* — Wayne J Dustman; Edward R Gimmi (57) ABSTRACT

This invention relates to crystalline forms of (R)-1-(1-(methylsulfonyl)propan-2-yl)-4-(trifluoromethyl)indoline-5-carbonitrile, a modulator of the androgen receptor, and methods for the use in treatment.

8 Claims, 6 Drawing Sheets

CRYSTALLINE FORMS

This application is the US National Stage of International Application No. PCT/IB2015/050440, filed 20 Jan. 2015 which claims benefit of the filing date of U.S. Provisional Application No. 61/929,814, filed 21 Jan. 2014, both of which are incorporated herein by reference in their entireties.

FIELD OF THE INVENTION

This invention relates to crystalline forms of (R)-1-(1-(methylsulfonyl)propan-2-yl)-4-(trifluoromethyl)indoline-5-carbonitrile, a modulator of the androgen receptor, and methods for the use in treatment.

BACKGROUND OF THE INVENTION

Steroidal nuclear receptor (NR) ligands are known to play important roles in the health of both men and women. Testosterone (T) and dihydrotestosterone (DHT) are endogenous steroidal ligands for the androgen receptor (AR) that appear to play a role in every tissue type found in the mammalian body. During the development of the fetus, androgens play a role in sexual differentiation and development of male sexual organs. Further sexual development is mediated by androgens during puberty. Androgens play diverse roles in the adult, including stimulation and maintenance of male sexual accessory organs and maintenance of the musculoskeletal system. Cognitive function, sexuality, aggression, and mood are some of the behavioral aspects mediated by androgens. Androgens have a physiologic effect on the skin, bone, and skeletal muscle, as well as blood, lipids, and blood cells (Chang, C. and Whipple, G. *Androgens and Androgen Receptors*. Kluwer Academic Publishers: Boston, Mass., 2002)

Many clinical studies with testosterone have demonstrated significant gains in muscle mass and function along with decreases in visceral fat. See, for example, Bhasin (2003) S. *J. Gerontol. A Biol. Sci. Med. Sci.* 58:1002-8, and Ferrando, A. A. et al. (2002) *Am. J. Phys. Endo. Met.* 282: E601-E607. Androgen replacement therapy (ART) in men improves body composition parameters such as muscle mass, strength, and bone mineral density (see, for example, Asthana, S. et al. (2004) *J. Ger., Series A: Biol. Sci. Med. Sci.* 59: 461-465). There is also evidence of improvement in less tangible parameters such as libido and mood. Andrologists and other specialists are increasingly using androgens for the treatment of the symptoms of androgen deficiency. ART, using T and its congeners, is available in transdermal, injectable, and oral dosage forms. All current treatment options have contraindications (e.g., prostate cancer) and side-effects, such as increased hematocrit, liver toxicity, and sleep apnoea. Side-effects from androgen therapy in women include: acne, hirsutism, and lowering of high-density lipoprotein (HDL) cholesterol levels, a notable side-effect also seen in men.

Agents that could selectively afford the benefits of androgens and greatly reduce the side-effect profile would be of great therapeutic value. Interestingly, certain NR ligands are known to exert their action in a tissue selective manner (see, for example, Smith et al. (2004) *Endoc. Rev.* 2545-71). This selectivity stems from the particular ability of these ligands to function as agonists in some tissues, while having no effect or even an antagonist effect in other tissues. The term "selective receptor modulator" (SRM) has been given to these molecules. A synthetic compound that binds to an intracellular receptor and mimics the effects of the native hormone is referred to as an agonist. A compound that inhibits the effect of the native hormone is called an antagonist. The term "modulators" refers to compounds that have a spectrum of activities ranging from full agonism to partial agonism to full antagonism.

SARMs (selective androgen receptor modulators) represent an emerging class of small molecule pharmacotherapeutics that have the potential to afford the important benefits of androgen therapy without the undesired side-effects. Many SARMs with demonstrated tissue-selective effects are currently in the early stages of development See, for example, Mohler, M. L. et al. (2009) *J. Med. Chem.* 52(12): 3597-617. One notable SARM molecule, Ostarine™, has recently completed phase I and II clinical studies. See, for example, Zilbermint, M. F. and Dobs, A. S. (2009) *Future Oncology* 5(8):1211-20. Ostarine™ appears to increase total lean body mass and enhance functional performance. Because of their highly-selective anabolic properties and demonstrated androgenic-sparing activities, SARMs should be useful for the prevention and/or treatment of many diseases in both men and women, including, but not limited to sarcopenia, cachexias (including those associated with cancer, heart failure, chronic obstructive pulmonary disease (COPD), and end stage renal disease (ESRD), urinary incontinence, osteoporosis, frailty, dry eye and other conditions associated with aging or androgen deficiency. See, for example, Ho et al. (2004) *Curr Opin Obstet Gynecol.* 16:405-9; Albaaj et al. (2006) *Postgrad Med J* 82:693-6; Caminti et al. (2009) *J Am Coll Cardiol.* 54(10):919-27; Iellamo et al. (2010) *J Am Coll Cardiol.* 56(16):1310-6; Svartberg (2010) *Curr Opin Endocrinol Diabetes Obes.* 17(3):257-61, and Mammadov et al. (2011) *Int Urol Nephrol* 43:1003-8. SARMS also show promise for use in promoting muscle regeneration and repair (see, for example, Serra et al. (Epub 2012 Apr. 12) doi:10.1093/Gerona/gls083), in the areas of hormonal male contraception and benign prostatic hyperplasia (BPH), and in wound healing (see, for example, Demling (2009) *ePlasty* 9:e9).

Preclinical studies and emerging clinical data demonstrate the therapeutic potential of SARMs to address the unmet medical needs of many patients. The demonstrated advantages of this class of compounds in comparison with steroidal androgens (e.g., tissue-selective activity, oral administration, AR selectivity, and lack of androgenic effect) position SARMs for a bright future of therapeutic applications.

Although amorphous forms of SARMs may be developed for some uses, compounds having high crystallinity are generally preferred for pharmaceutical use due to their improved solubility and stability. Accordingly, there remains a need in the art for crystalline form of SARMs for therapeutic use.

BRIEF SUMMARY OF INVENTION

The present invention relates to crystalline forms of non-steroidal compounds that are modulators of androgen receptor, and also to the use of these compounds in therapy.

The present invention provides a crystalline form of (R)-1-(1-(methylsulfonyl)propan-2-yl)-4-(trifluoromethyl) indoline-5-carbonitrile. In a preferred embodiment the crystalline form of (R)-1-(1-(methylsulfonyl)propan-2-yl)-4-(trifluoromethyl)indoline-5-carbonitrile is anhydrous.

According to one aspect of the invention, the crystalline form of anhydrous (R)-1-(1-(methylsulfonyl)propan-2-yl)-4-(trifluoromethyl)indoline-5-carbonitrile is Form 1.

In a particular embodiment, Form 1 of (R)-1-(1-(methylsulfonyl)propan-2-yl)-4-(trifluoromethyl)indoline-5-carbonitrile is characterized by an X-ray powder diffraction (XRPD) pattern that has the representative peaks:

| Position [°2Theta] | d-spacing [Å] |
|---|---|
| 9.2 ± 0.1 | 9.6 |
| 11.4 ± 0.1 | 7.8 |
| 11.9 ± 0.1 | 7.4 |
| 13.8 ± 0.1 | 6.4 |
| 15.4 ± 0.1 | 5.7 |
| 17.8 ± 0.1 | 5.0 |
| 18.0 ± 0.1 | 4.9 |
| 18.5 ± 0.1 | 4.8 |
| 18.7 ± 0.1 | 4.7 |
| 23.2 ± 0.1 | 3.8 |

Figure 1:
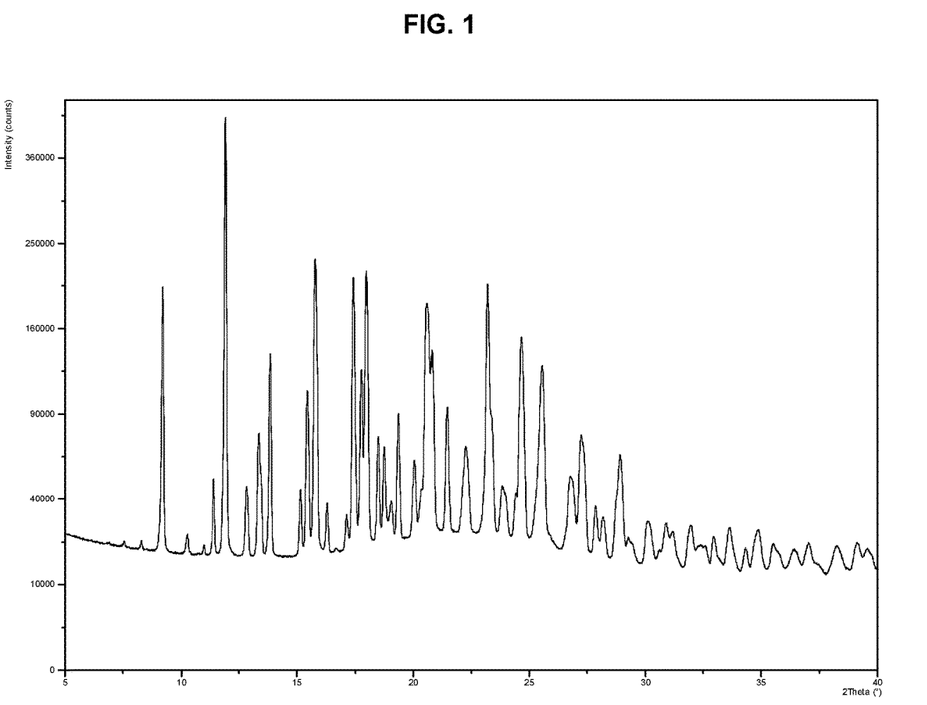
FIG. 1 depicts the XRPD of crystalline form 1 of anhydrous (R)-1-(1-(methylsulfonyl)propan-2-yl)-4-(trifluoromethyl)indoline-5-carbonitrile.

In another embodiment, Form 1 of (R)-1-(1-(methylsulfonyl)propan-2-yl)-4-(trifluoromethyl)indoline-5-carbonitrile is characterized by an XRPD pattern substantially in accordance with FIG. 1.

In an additional embodiment, Form 1 of (R)-1-(1-(methylsulfonyl)propan-2-yl)-4-(trifluoromethyl)indoline-5-carbonitrile is characterized by an $^{19}$F SSNMR (solid state nuclear magnetic resonance) spectrum comprising isotropic chemical shifts at −52.7±0.2, −56.0±0.2 and −57.1±0.2 ppm, wherein the $^{19}$F SSNMR spectrum is obtained on a spectrometer operating at a frequency of 470.40 MHz for $^{19}$F observation using a cross-polarization pulse sequence with a Bruker 4-mm triple resonance magic-angle spinning probe at a rotor frequency of 12.5 kHz.

Figure 4:
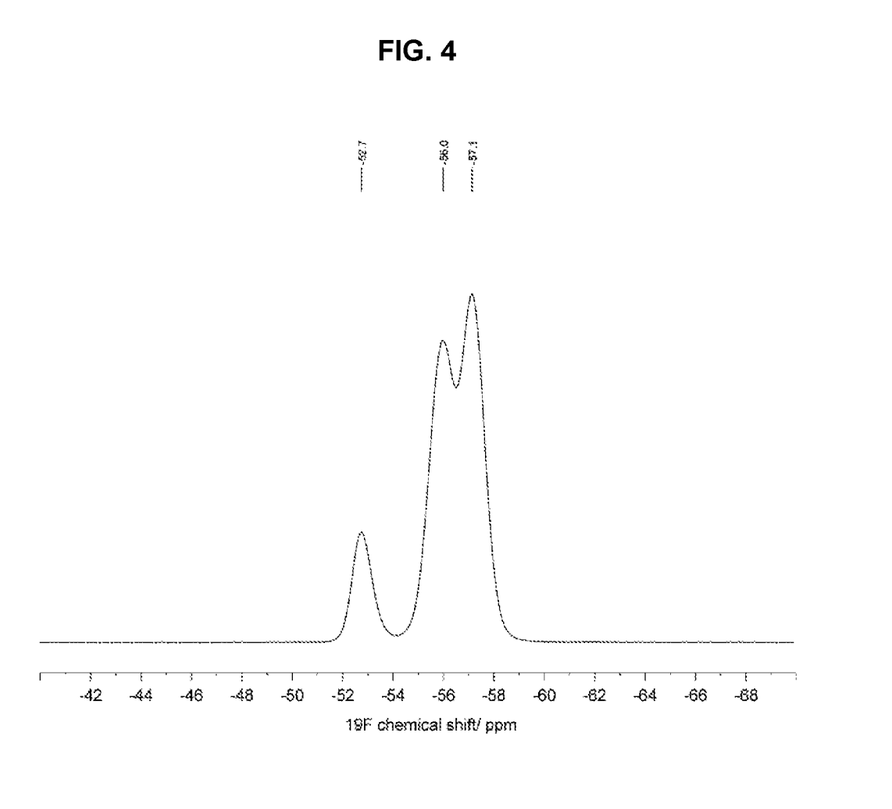
FIG. 4 depicts the isotropic region of the $^{19}$F solid state NMR (SSNMR) spectrum of the compound of crystalline form 1 of anhydrous (R)-1-(1-(methylsulfonyl)propan-2-yl)-4-(trifluoromethyl)indoline-5-carbonitrile. The solid state NMR spectrum was obtained on a spectrometer operating at a frequency of 470.40 MHz for $^{19}$F observation and a spinning speed of 12.5 kHz, according to the procedures described herein. The $^{19}$F resonance at 52.7 ppm is likely the result of site disorder in the crystal structure.

In one embodiment, Form 1 of (R)-1-(1-(methylsulfonyl)propan-2-yl)-4-(trifluoromethyl)indoline-5-carbonitrile is characterized by an $^{19}$F SSNMR spectrum substantially in accordance with FIG. 4.

In an additional embodiment, Form 1 of (R)-1-(1-(methylsulfonyl)propan-2-yl)-4-(trifluoromethyl)indoline-5-carbonitrile is characterized by an $^{13}$C SSNMR (solid state nuclear magnetic resonance) spectrum comprising isotropic chemical shifts at 140.1±0.2, 136.9±0.2, 134.9±0.2, 130.4±0.2, 128.5±0.2, 126.6±0.2, 126.0±0.2, 125.7±0.2, 124.8±0.2, 121.9±0.2, 120.9±0.2, 119.7±0.2, 118.6±0.2, 115.5±0.2, 115.1±0.2, 103.6±0.2, 100.3±0.2, 98.9±0.2, 58.1±0.2, 55.7±0.2, 54.7±0.2, 51.1±0.2, 50.4±0.2, 44.7±0.2, 43.6±0.2, 40.7±0.2, 23.5±0.2 and 20.7±0.2 ppm, wherein the $^{13}$C SSNMR spectrum is obtained on a spectrometer operating at a frequency of 125.73 MHz for $^{13}$C observation using a cross-polarization pulse sequence with a Bruker 4-mm triple resonance magic-angle spinning probe at a rotor frequency of 8 kHz.

Figure 3:
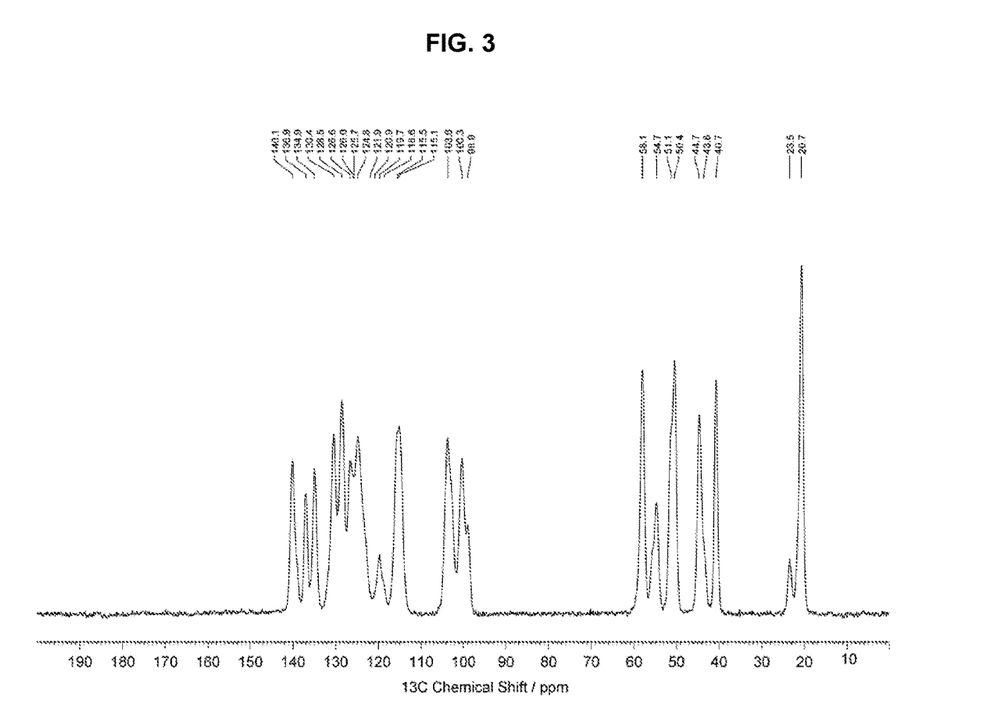
FIG. 3 depicts the $^{13}$C solid state NMR (SSNMR) spectrum of crystalline form 1 of anhydrous (R)-1-(1-(methylsulfonyl)propan-2-yl)-4-(trifluoromethyl)indoline-5-carbonitrile. The solid state NMR spectrum was obtained on a spectrometer operating at a frequency of 125.73 MHz for $^{13}$C observation and a spinning speed of 8 kHz, according to the procedures described herein. The 119.7 ppm carbon site is split by the $^1J_{C-F}$ coupling, and the carbon sites at 55.7, 43.6, and 23.5 ppm are likely the result of site disorder in the crystal structure.

In certain embodiments, Form 1 of (R)-1-(1-(methylsulfonyl)propan-2-yl)-4-(trifluoromethyl)indoline-5-carbonitrile is characterized by an $^{13}$C SSNMR spectrum substantially in accordance with FIG. 3.

According to another aspect of the invention, the crystalline form of (R)-1-(1-(methylsulfonyl)propan-2-yl)-4-(trifluoromethyl)indoline-5-carbonitrile is Form 2.

In one embodiment, Form 2 of (R)-1-(1-(methylsulfonyl)propan-2-yl)-4-(trifluoromethyl)indoline-5-carbonitrile is characterized by an X-ray powder diffraction (XRPD) pattern that has the representative peaks:

| Position [°2Theta] | d-spacing [Å] |
|---|---|
| 7.4 ± 0.1 | 11.9 |
| 12.7 ± 0.1 | 7.0 |
| 17.5 ± 0.1 | 5.1 |
| 19.5 ± 0.1 | 4.6 |
| 21.9 ± 0.1 | 4.1 |
| 22.5 ± 0.1 | 3.9 |
| 23.9 ± 0.1 | 3.7 |
| 26.5 ± 0.1 | 3.4 |

Figure 2:
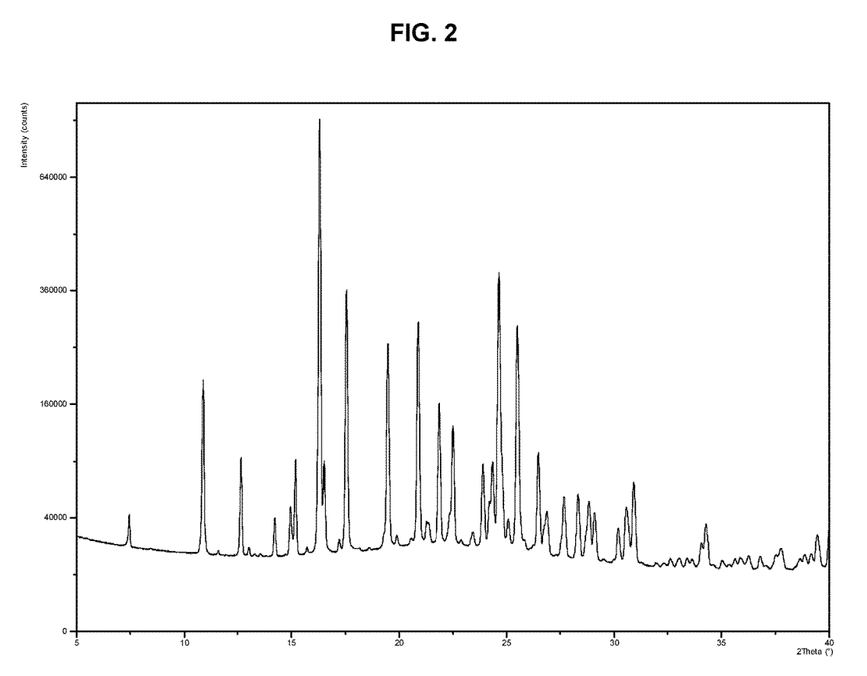
FIG. 2 depicts the XRPD of crystalline form 2 of anhydrous (R)-1-(1-(methylsulfonyl)propan-2-yl)-4-(trifluoromethyl)indoline-5-carbonitrile.

In another embodiment, Form 2 of (R)-1-(1-(methylsulfonyl)propan-2-yl)-4-(trifluoromethyl)indoline-5-carbonitrile is characterized by an XRPD pattern substantially in accordance with FIG. 2.

In an additional embodiment, Form 2 of (R)-1-(1-(methylsulfonyl)propan-2-yl)-4-(trifluoromethyl)indoline-5-carbonitrile is characterized by an $^{19}$F SSNMR spectrum comprising isotropic chemical shifts at −55.5±0.2 and −56.3±0.2 ppm, wherein the $^{19}$F SSNMR spectrum is obtained on a spectrometer operating at a frequency of 470.40 MHz for $^{19}$F observation using a cross-polarization pulse sequence with a Bruker 4-mm triple resonance magic-angle spinning probe at a rotor frequency of 12.5 kHz.

Figure 6:
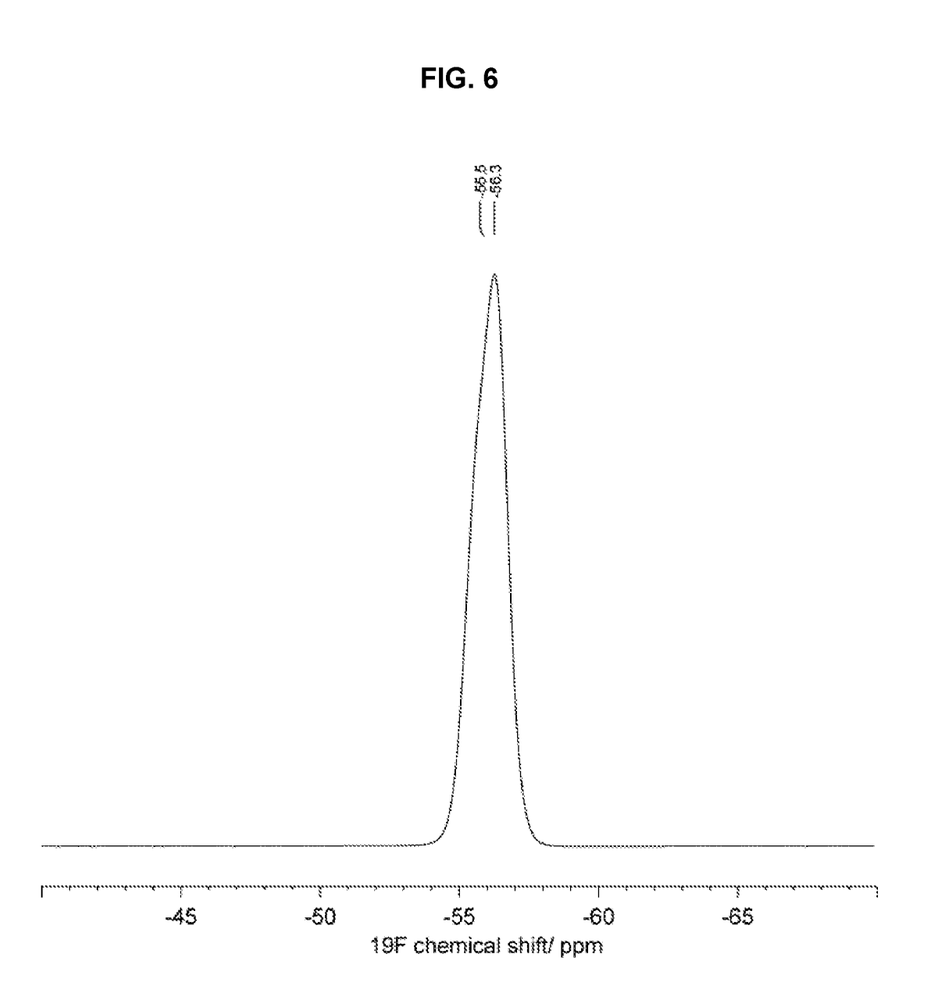
FIG. 6 depicts the isotropic region of the $^{19}$F solid state NMR (SSNMR) spectrum of crystalline form 2 of anhydrous (R)-1-(1-(methylsulfonyl)propan-2-yl)-4-(trifluoromethyl)indoline-5-carbonitrile. The solid state NMR spectrum was obtained on a spectrometer operating at a frequency of 470.40 MHz for $^{19}$F observation and a spinning speed of 12.5 kHz, according to the procedures described herein

According to one embodiment, Form 2 of (R)-1-(1-(methylsulfonyl)propan-2-yl)-4-(trifluoromethyl)indoline-5-carbonitrile is characterized by an $^{19}$F SSNMR spectrum substantially in accordance with FIG. 6.

According to another embodiment, Form 2 of (R)-1-(1-(methylsulfonyl)propan-2-yl)-4-(trifluoromethyl)indoline-5-carbonitrile is characterized by an $^{13}$C SSNMR (solid state nuclear magnetic resonance) spectrum comprising isotropic chemical shifts at 138.4±0.2, 127.4±0.2, 125.5±0.2, 124.3±0.2, 123.3±0.2 116.5±0.2, 114.1±0.2, 104.7±0.2, 97.4±0.2, 61.8±0.2, 60.9±0.2, 59.2±0.2, 48.2±0.2, 47.6±0.2, 46.3±0.2, 44.4±0.2, 42.3±0.2, and 26.1±0.2 ppm, wherein the $^{13}$C SSNMR spectrum is obtained on a spectrometer operating at a frequency of 125.73 MHz for $^{13}$C observation using a cross-polarization pulse sequence with a Bruker 4-mm triple resonance magic-angle spinning probe at a rotor frequency of 8 kHz.

Figure 5:
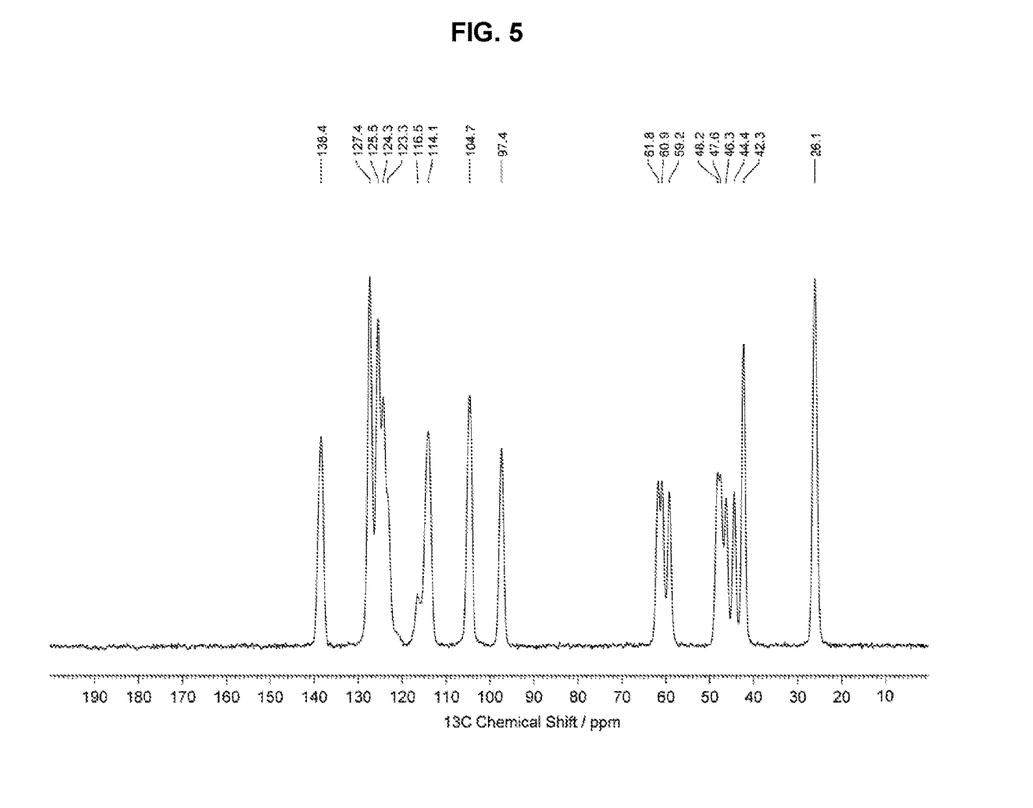
FIG. 5 depicts the $^{13}$C solid state NMR (SSNMR) spectrum of the compound of crystalline form 2 of anhydrous (R)-1-(1-(methylsulfonyl)propan-2-yl)-4-(trifluoromethyl)indoline-5-carbonitrile. The solid state NMR spectrum was obtained on a spectrometer operating at a frequency of 125.73 MHz for $^{13}$C observation and a spinning speed of 8 kHz, according to the procedures described herein. The 116.5 ppm peak arises from a carbon site, split by the $^1J_{C-F}$ coupling.

In an additional embodiment, Form 2 of (R)-1-(1-(methylsulfonyl)propan-2-yl)-4-(trifluoromethyl)indoline-5-carbonitrile is characterized by an $^{13}$C SSNMR spectrum substantially in accordance with FIG. 5.

Another aspect of the present invention provides a pharmaceutical composition comprising a crystalline form of the present invention and one or more pharmaceutically acceptable excipients.

Another aspect of the present invention provides a crystalline form of the present invention for use as an active therapeutic substance.

Another aspect of the present invention provides a crystalline form of the present invention for use in the acceleration of wound healing and burn healing and the treatment of hypogonadism, sarcopenia, osteoporosis, muscle wasting, wasting diseases, cachexia (including cachexias associated with cancer, chronic obstructive pulmonary disease (COPD), end stage renal disease (ESRD), heart failure, HIV illness, HIV treatment, and diabetes mellitus type 1 and type 2), frailty, dry eye, prostatic hyperplasia, prostate cancer, breast cancer, menopausal and andropausal vasomotor conditions, sexual dysfunction, erectile dysfunction, depression, uterine fibroid disease, endometriosis, urinary incontinence (including urinary incontinence associated with muscle and/or tissue wasting of the pelvic floor), acne, hirsutism, male contraception, impotence, and in the use as male and female hormone replacement therapy, as a stimulant of hematopoiesis, and as an anabolic agent.

Another aspect of the present invention provides the use of a crystalline form of the present invention in the manufacture of a medicament for use in the acceleration of wound healing and the treatment of hypogonadism, sarcopenia, osteoporosis, muscle wasting, wasting diseases, muscle wasting and cachexia (including muscle wasting and cachexias associated with cancer, chronic obstructive pulmonary disease (COPD), end stage renal disease (ESRD), heart failure, HIV illness, HIV treatment, and diabetes mellitus type 1 and type 2), frailty, dry eye, prostatic hyperplasia, prostate cancer, breast cancer, menopausal and andropausal vasomotor conditions, urinary incontinence (including urinary incontinence associated with muscle and/or tissue wasting of the pelvic floor), sexual dysfunction, erectile dysfunction, depression, uterine fibroid disease, endometriosis, acne, hirsutism, male contraception, impotence, and in the use as male and female hormone replacement therapy, as a stimulant of hematopoiesis, and as an anabolic agent.

Another aspect of the present invention provides a method for the treatment of hypogonadism, sarcopenia, osteoporosis, muscle wasting, wasting diseases, cachexia and muscle wasting (including muscle wasting and cachexias associated with cancer, chronic obstructive pulmonary disease (COPD), end stage renal disease (ESRD), heart failure, HIV illness, HIV treatment, and diabetes mellitus type 1 and type 2), frailty, prostatic hyperplasia, prostate cancer, breast cancer, menopausal and andropausal vasomotor conditions, chronic obstructive pulmonary disease (COPD), urinary incontinence (including urinary incontinence associated with muscle and/or tissue wasting of the pelvic floor), sexual dysfunction, erectile dysfunction, depression, uterine fibroid disease, endometriosis, acne, hirsutism, male contraception, impotence, and a method of male and female hormone replacement therapy, stimulation of hematopoiesis, and anabolism, wherein the method comprises administration of a crystalline form of the present invention.

In another aspect, the present invention provides a method for the treatment of a muscle injury, and for accelerating muscle repair comprising the administration of a crystalline form of the present invention. Also provided is the use of a crystalline form of the present invention in the treatment of a muscle injury, or in the acceleration of muscle repair. Additionally included is the use of a crystalline form of the present invention in the manufacture of a medicament for the treatment of muscle injury or the acceleration of muscle repair.

DETAILED DESCRIPTION OF THE INVENTION

The present invention provides a crystalline form of (R)-1-(1-(methylsulfonyl)propan-2-yl)-4-(trifluoromethyl)indoline-5-carbonitrile:

In a particular embodiment, wherein the crystalline form of (R)-1-(1-(methylsulfonyl)propan-2-yl)-4-(trifluoromethyl)indoline-5-carbonitrile is anhydrous. In a specific embodiment, the anhydrous crystalline form has a water content of less than 1.5, preferably less than 1.0, more preferably less than 0.5 percent by weight.

According to one aspect of the invention, the crystalline form of (R)-1-(1-(methylsulfonyl)propan-2-yl)-4-(trifluoromethyl)indoline-5-carbonitrile is Form 1.

In a particular embodiment, the crystalline form of (R)-1-(1-(methylsulfonyl)propan-2-yl)-4-(trifluoromethyl)indoline-5-carbonitrile is characterized by an X-ray powder diffraction (XRPD) pattern that has the representative peaks:

| Position [°2Theta] | d-spacing [Å] |
|---|---|
| 9.2 ± 0.1 | 9.6 |
| 11.4 ± 0.1 | 7.8 |
| 11.9 ± 0.1 | 7.4 |
| 13.8 ± 0.1 | 6.4 |
| 15.4 ± 0.1 | 5.7 |
| 17.8 ± 0.1 | 5.0 |
| 18.0 ± 0.1 | 4.9 |
| 18.5 ± 0.1 | 4.8 |
| 18.7 ± 0.1 | 4.7 |
| 23.2 ± 0.1 | 3.8 |

In another embodiment, the crystalline form of (R)-1-(1-(methylsulfonyl)propan-2-yl)-4-(trifluoromethyl)indoline-5-carbonitrile is characterized by an XRPD pattern substantially in accordance with FIG. 1.

In one embodiment, the crystalline form of (R)-1-(1-(methylsulfonyl)propan-2-yl)-4-(trifluoromethyl)indoline-5-carbonitrile is characterized by an $^{19}$F SSNMR (solid state nuclear magnetic resonance) spectrum comprising isotropic chemical shifts at −56.0±0.5 and −57.1±0.5 ppm, wherein the $^{19}$F SSNMR spectrum is obtained on a spectrometer operating at a frequency of 470.40 MHz for $^{19}$F observation using a cross-polarization pulse sequence with a Bruker 4-mm triple resonance magic-angle spinning probe at a rotor frequency of 12.5 kHz.

In an additional embodiment, the crystalline form of (R)-1-(1-(methylsulfonyl)propan-2-yl)-4-(trifluoromethyl)indoline-5-carbonitrile is characterized by an $^{19}$F SSNMR (solid state nuclear magnetic resonance) spectrum comprising isotropic chemical shifts at −52.7±0.2, −56.0±0.2 and −57.1±0.2 ppm, wherein the $^{19}$F SSNMR spectrum is obtained on a spectrometer operating at a frequency of 470.40 MHz for $^{19}$F observation using a cross-polarization pulse sequence with a Bruker 4-mm triple resonance magic-angle spinning probe at a rotor frequency of 12.5 kHz.

In one embodiment, the crystalline form of (R)-1-(1-(methylsulfonyl)propan-2-yl)-4-(trifluoromethyl)indoline-5-carbonitrile is characterized by an $^{19}$F SSNMR spectrum substantially in accordance with FIG. 4.

In one embodiment, the crystalline form of (R)-1-(1-(methylsulfonyl)propan-2-yl)-4-(trifluoromethyl)indoline-5-carbonitrile is characterized by an $^{13}$C SSNMR (solid state nuclear magnetic resonance) spectrum comprising isotropic chemical shifts at 140.1±0.2, 136.9±0.2, 134.9±0.2, 130.4±0.2, 128.5±0.2, 126.6±0.2, 124.8±0.2, 119.7±0.2, 118.6±0.2, 115.5±0.2, 115.1±0.2, 103.6±0.2, 100.3±0.2, 98.9±0.2, 58.1±0.2, 54.7±0.2, 51.1±0.2, 50.4±0.2, 44.7±0.2, 40.7±0.2, and 20.7±0.2 ppm, wherein the $^{13}$C SSNMR spectrum is obtained on a spectrometer operating at a frequency of 125.73 MHz for $^{13}$C observation using a cross-polarization pulse sequence with a Bruker 4-mm triple resonance magic-angle spinning probe at a rotor frequency of 8 kHz.

In an additional embodiment, the crystalline form of (R)-1-(1-(methylsulfonyl)propan-2-yl)-4-(trifluoromethyl)indoline-5-carbonitrile is characterized by an $^{13}$C SSNMR (solid state nuclear magnetic resonance) spectrum comprising isotropic chemical shifts at 140.1±0.2, 136.9±0.2, 134.9±0.2, 130.4±0.2, 128.5±0.2, 126.6±0.2, 126.0±0.2, 125.7±0.2, 124.8±0.2, 121.9±0.2, 120.9±0.2, 119.7±0.2, 118.6±0.2, 115.5±0.2, 115.1±0.2, 103.6±0.2, 100.3±0.2, 98.9±0.2, 58.1±0.2, 55.7±0.2, 54.7±0.2, 51.1±0.2, 50.4±0.2, 44.7±0.2, 43.6±0.2, 40.7±0.2, 23.5±0.2 and 20.7±0.2 ppm, wherein the $^{13}$C SSNMR spectrum is obtained on a spectrometer operating at a frequency of 125.73 MHz for $^{13}$C observation using a cross-polarization pulse sequence with a Bruker 4-mm triple resonance magic-angle spinning probe at a rotor frequency of 8 kHz.

In a certain embodiment, the crystalline form of (R)-1-(1-(methylsulfonyl)propan-2-yl)-4-(trifluoromethyl)indoline-5-carbonitrile is characterized by an $^{13}$C SSNMR spectrum substantially in accordance with FIG. 3.

According to another aspect of the invention, the crystalline form of (R)-1-(1-(methylsulfonyl)propan-2-yl)-4-(trifluoromethyl)indoline-5-carbonitrile is Form 2.

In one embodiment, the crystalline form of (R)-1-(1-(methylsulfonyl)propan-2-yl)-4-(trifluoromethyl)indoline-5-carbonitrile is characterized by an X-ray powder diffraction (XRPD) pattern that has the representative peaks:

| Position [°2Theta] | d-spacing [Å] |
|---|---|
| 7.4 ± 0.1 | 11.9 |
| 12.7 ± 0.1 | 7.0 |
| 17.5 ± 0.1 | 5.1 |
| 19.5 ± 0.1 | 4.6 |
| 21.9 ± 0.1 | 4.1 |
| 22.5 ± 0.1 | 3.9 |
| 23.9 ± 0.1 | 3.7 |
| 26.5 ± 0.1 | 3.4 |

In another embodiment, the crystalline form of (R)-1-(1-(methylsulfonyl)propan-2-yl)-4-(trifluoromethyl)indoline-5-carbonitrile is characterized by an XRPD pattern substantially in accordance with FIG. 2.

In an additional embodiment, the crystalline form of (R)-1-(1-(methylsulfonyl)propan-2-yl)-4-(trifluoromethyl)indoline-5-carbonitrile is characterized by an $^{19}$F SSNMR spectrum comprising isotropic chemical shifts at −55.5±0.2 and −56.3±0.2 ppm, wherein the $^{19}$F SSNMR spectrum is obtained on a spectrometer operating at a frequency of 470.40 MHz for $^{19}$F observation using a cross-polarization pulse sequence with a Bruker 4-mm triple resonance magic-angle spinning probe at a rotor frequency of 12.5 kHz.

In another embodiment, the crystalline form of (R)-1-(1-(methylsulfonyl)propan-2-yl)-4-(trifluoromethyl)indoline-5-carbonitrile is characterized by an $^{19}$F SSNMR spectrum comprising isotropic chemical shifts at −55.5±0.5 and −56.3±0.5 ppm, wherein the $^{19}$F SSNMR spectrum is obtained on a spectrometer operating at a frequency of 470.40 MHz for $^{19}$F observation using a cross-polarization pulse sequence with a Bruker 4-mm triple resonance magic-angle spinning probe at a rotor frequency of 12.5 kHz.

According to one embodiment, the crystalline form of (R)-1-(1-(methylsulfonyl)propan-2-yl)-4-(trifluoromethyl)indoline-5-carbonitrile is characterized by an $^{19}$F SSNMR spectrum substantially in accordance with FIG. 6.

According to another embodiment, the crystalline form of (R)-1-(1-(methylsulfonyl)propan-2-yl)-4-(trifluoromethyl)indoline-5-carbonitrile is characterized by an $^{13}$C SSNMR (solid state nuclear magnetic resonance) spectrum comprising isotropic chemical shifts at 138.4±0.2, 127.4±0.2, 125.5±0.2, 124.3±0.2, 123.3±0.2 116.5±0.2, 114.1±0.2, 104.7±0.2, 97.4±0.2, 61.8±0.2, 60.9±0.2, 59.2±0.2, 48.2±0.2, 47.6±0.2, 46.3±0.2, 44.4±0.2, 42.3±0.2, and 26.1±0.2 ppm, wherein the $^{13}$C SSNMR spectrum is obtained on a spectrometer operating at a frequency of 125.73 MHz for $^{13}$C observation using a cross-polarization pulse sequence with a Bruker 4-mm triple resonance magic-angle spinning probe at a rotor frequency of 8 kHz.

In an additional embodiment, the crystalline form of (R)-1-(1-(methylsulfonyl)propan-2-yl)-4-(trifluoromethyl)

indoline-5-carbonitrile is characterized by an $^{13}$C SSNMR spectrum substantially in accordance with FIG. 5.

Another aspect of the present invention provides a pharmaceutical composition comprising a crystalline form of the present invention and one or more pharmaceutically acceptable excipients. In a preferred embodiment, the crystalline form in Form 1.

It is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1 or 2 provided herein is an XRPD pattern that would be considered by one skilled in the art to represent a compound possessing the same crystal form as the compound that provided the XRPD pattern of FIG. 1 or 2. That is, the XRPD pattern may be identical to that of FIG. 1 or 2, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of (R)-1-(1-(methylsulfonyl)propan-2-yl)-4-(trifluoromethyl)indoline-5-carbonitrile, with FIG. 1 or 2 and, using expertise and knowledge in the art, readily determine whether the XRPD pattern of the sample is substantially in accordance with the XRPD pattern shown in the figure. If the XRPD pattern is substantially in accordance with FIG. 1 (Form 1) or 2 (Form 2), the sample form can be readily and accurately identified as having the same form as Form 1 or Form 2 of (R)-1-(1-(methylsulfonyl)propan-2-yl)-4-(trifluoromethyl)indoline-5-carbonitrile.

Further, it is also well known and understood to those skilled in the art that the apparatus employed, humidity, temperature, orientation of the powder crystals, and other parameters involved in obtaining an SSNMR spectrum may cause some variability in the appearance, intensities, and positions of the peaks in the spectrum. A SSNMR spectrum that is "substantially in accordance" with that of FIG. 3, 4, 5, or 6 provided herein is an SSNMR spectrum that would be considered by one skilled in the art to represent a compound possessing the same crystal form as the compound that provided the SSNMR spectrum of FIG. 3, 4, 5, or 6. That is, the SSNMR spectrum may be identical to that of FIG. 3, 4, 5, or 6, or more likely it may be somewhat different. Such a SSNMR spectrum may not necessarily show each of the chemical shifts of any one of the spectra presented herein, and/or may show a slight change in appearance, intensity, or a shift in position of said chemical shift resulting from differences in the conditions involved in obtaining the data. A person skilled in the art is capable of determining if a sample of a crystalline compound has the same form as, or a different form from, a form disclosed herein by comparison of their SSNMR spectra. For example, one skilled in the art can overlay an SSNMR spectrum of a sample of (R)-1-(1-(methylsulfonyl)propan-2-yl)-4-(trifluoromethyl)indoline-5-carbonitrile with FIG. 3, 4, 5, or 6 and, using expertise and knowledge in the art, readily determine whether the SSNMR spectrum of the sample is substantially in accordance with the SSNMR spectrum of Compound B—anhydrous crystalline form. If the SSNMR spectrum is substantially in accordance with 3 (Form 1), 4 (Form 1), 5 (Form 2), or 6 (Form 2), the sample form can be readily and accurately identified as having the same form as that having a substantially similar spectrum as shown in the respective figure.

The crystalline forms of the present invention are believed to modulate the function of one or more nuclear hormone receptor(s). Particularly, the crystalline forms of the present invention modulate the androgen receptor ("AR"). The present invention includes crystalline forms that are selective agonists, partial agonists, antagonists, or partial antagonists of the AR. Crystalline forms of the present invention are useful in the treatment of AR-associated diseases and conditions, for example, a disease or condition that is prevented, alleviated, or cured through the modulation of the function or activity of AR. Such modulation may be isolated within certain tissues or widespread throughout the body of the subject being treated.

As used herein, the term "treatment" refers to alleviating the specified condition, eliminating or reducing the symptoms of the condition, slowing or eliminating the progression of the condition.

The crystalline forms of the present invention may also be useful in preventing or delaying the initial occurrence of the condition in a subject, or reoccurrence of the condition in a previously afflicted subject.

One embodiment of the present invention provides crystalline forms of the present invention for use in medical therapy. Particularly, the present invention provides for the treatment of disorders mediated by androgenic activity. More particularly, the present invention provides treatment of disorders responsive to tissue-selective anabolic and or androgenic activity. A further embodiment of the invention provides a method of treatment of a mammal suffering from a disorder mediated by androgenic activity, which includes administering to said subject an effective amount of a crystalline form of the present invention.

The crystalline forms of the present invention may find use for the treatment of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline (ARFD), dry eye, sarcopenia, end-stage renal disease (ESRD), chronic fatigue syndrome, chronic myalgia, acute fatigue syndrome, sepsis, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence, atherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstrual syndrome, contraception, uterine fibroid disease, aortic smooth muscle cell proliferation, male hormone replacement, or ADAM.

A further embodiment of the invention provides a method of treatment of a mammal requiring the treatment of a variety of disorders including, but not limited to, osteoporosis and/or the prevention of reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline (ARFD), dry eye, sarcopenia, end-stage renal disease (ESRD), chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, malignant tumor cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, menopausal vasomotor conditions, urinary incontinence (including urinary incontinence associated with muscle and/or tissue wasting of the pelvic floor), atherosclerosis, libido enhancement, sexual dysfunction, depression, nervousness, irritability, stress, reduced mental energy and low self-esteem, improvement of cognitive function, endometriosis, polycystic ovary syndrome, counteracting preeclampsia, premenstrual syndrome, contraception, uterine fibroid disease, aortic smooth muscle cell proliferation, male hormone replacement, or ADAM. Preferably the crystalline forms of the present invention are used as male and female hormone replacement therapy or for the treatment or prevention of hypogonadism, osteoporosis, muscle wasting, wasting diseases, cancer cachexia, frailty, prostatic hyperplasia, prostate cancer, breast cancer, menopausal and andropausal vasomotor conditions, urinary incontinence, sexual dysfunction, erectile dysfunction, depression, uterine fibroid disease, and/or endometriosis, treatment of acne, hirsutism, stimulation of hematopoiesis, male contraception, impotence, and as anabolic agents, which use includes administering to a subject an effective amount of a crystalline form of the present invention.

In some embodiments, the invention encompasses the use of a crystalline form of the invention in the treatment of muscle injury. In particular embodiments, the muscle injury is a surgery-related muscle injury, a traumatic muscle injury, a work-related skeletal muscle injury, or an overtraining-related muscle injury.

Non-limiting examples of surgery-related muscle injuries include muscle damage due to knee replacement, anterior cruciate ligament (ACL) repair, plastic surgery, hip replacement surgery, joint replacement surgery, tendon repair surgery, surgical repair of rotator cuff disease and injury, and amputation.

Non-limiting examples of traumatic muscle injuries include battlefield muscle injuries, auto accident-related muscle injuries, and sports-related muscle injuries. Traumatic injury to the muscle can include lacerations, blunt force contusions, shrapnel wounds, muscle pulls or tears, burns, acute strains, chronic strains, weight or force stress injuries, repetitive stress injuries, avulsion muscle injury, and compartment syndrome.

In one embodiment, the muscle injury is a traumatic muscle injury and the treatment method provides for administration of at least one high dose of a crystalline form of the invention immediately after the traumatic injury (for example, within one day of the injury) followed by periodic administration of a low dose of a crystalline form of the invention during the recovery period.

Non-limiting examples of work-related muscle injuries include injuries caused by highly repetitive motions, forceful motions, awkward postures, prolonged and forceful mechanical coupling between the body and an object, and vibration.

Overtraining-related muscle injuries include unrepaired or under-repaired muscle damage coincident with a lack of recovery or lack of an increase of physical work capacity.

In an additional embodiment, the muscle injury is exercise or sports-induced muscle damage resulting including exercise-induced delayed onset muscle soreness (DOMS).

In another aspect, the invention provides a method of treating a muscle degenerative disorder comprising administering to a human a crystalline form of the invention.

In particular embodiments, the muscle degenerative disorder is muscular dystrophy, myotonic dystrophy, polymyositis, or dermatomyositis.

For example, the methods may be used to treat a muscular dystrophy disorder selected from Duchenne MD, Becker MD, Congenital MD (Fukuyama), Emery Dreifuss MD, Limb girdle MD, and Fascioscapulohumeral MD.

The methods of the invention may also be used to treat myotonic dystrophy type I (DM1 or Steinert's), myotonic dystrophy type II (DM2 or proximal myotonic myopathy), or congenital myotonia.

In some embodiments, the invention encompasses a therapeutic combination in which the crystalline form of the invention is administered in a subject in combination with the implantation of a biologic scaffold (e.g., a scaffold comprising extracellular matrix) that promotes muscle regeneration. Such scaffolds are known in the art. See, for example, Turner and Badylack (2012) Cell Tissue Res. 347(3):759-74 and U.S. Pat. No. 6,576,265. Scaffolds comprising non-crosslinked extracellular matrix material are preferred.

In another aspect, the invention provides a method of treating tendon damage where the method comprises administering a crystalline form of the invention to a subject in need thereof. In a particular embodiment, the invention includes a method of enhancing the formation of a stable tendon-bone interface. In a related embodiment, the invention provides a method of increasing the stress to failure of tendons, for example surgically-repaired tendons. In an additional embodiment, the invention provides a method of reducing fibrosis at the repair site for surgically-repaired tendons. In a particular embodiment, the invention provides a method of treating tendon damage associated with rotator cuff injury, or tendon damage associated with surgical repair of rotator cuff injury. The mammal requiring treatment with a crystalline form of the present invention is typically a human being.

In one preferred embodiment, the disorder to be treated is muscle wasting associated with chronic obstructive pulmonary disease (COPD).

In another preferred embodiment, the disorder to be treated is muscle wasting associated with chronic kidney disease (CKD) or end stage renal disease (ESRD).

In an alternate preferred embodiment, the disorder to be treated is muscle wasting associated with chronic heart failure (CHF).

In an additional preferred embodiment, the crystalline form is used to accelerate bone fracture repair and healing, for example to accelerate the repair and healing of a hip fracture.

In yet another preferred embodiment, the crystalline form is used to treat urinary incontinence (including urinary incontinence associated with muscle and/or tissue wasting of the pelvic floor).

Typically, an effective amount, particularly a therapeutically effective amount of the crystalline form is administered according to the methods of the invention. As used herein, the term "effective amount" means that amount of a drug or pharmaceutical agent that will elicit the biological or medical response of a tissue, system, animal, or human that is being sought, for instance, by a researcher or clinician. The biological or medical response may be considered a prophylactic response or a treatment response.

The term "therapeutically effective amount" means any amount which, as compared to a corresponding subject who has not received such amount, results in improved treatment, healing or amelioration of a disease, disorder, or side effect, or a decrease in the rate of advancement of a disease or disorder. The term also includes within its scope amounts effective to enhance normal physiological function. For use in therapy, therapeutically effective amounts of a crystalline form may be administered as the raw chemical. Additionally, the active ingredient may be presented as a pharmaceutical composition.

Accordingly, the invention further provides pharmaceutical compositions that include effective amounts of crystalline forms of the present invention and one or more pharmaceutically acceptable carriers, diluents, or excipients. The crystalline forms of the present invention are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a crystalline form of the present invention with one or more pharmaceutically acceptable carriers, diluents or excipients.

A therapeutically effective amount of a crystalline form of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. An effective amount of a crystalline form of the present invention for the treatment of humans suffering from disorders such as frailty, generally, should be in the range of 0.01 to 100 mg/kg body weight of recipient (mammal) per day. More usually the effective amount should be in the range of 0.001 to 1 mg/kg body weight per day. Thus, for a 70 kg adult mammal the actual amount per day would usually be from 0.07 to 70 mg, such as 0.1-20 mg, for example 1-10 mg. This amount may be given in a single dose per day or in a number (such as two, three, four, five, or more) of sub-doses per day such that the total daily dose is the same.

Pharmaceutical formulations may be presented in unit dose forms containing a predetermined amount of active ingredient per unit dose. Such a unit may contain, as a non-limiting example, 0.1 mg to 100 mg of a crystalline form of the present invention, such as 0.1-50 mg, for example 0.5-15 mg depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component may be combined with an oral, non-toxic pharmaceutically acceptable inert carrier such as ethanol, glycerol, water, and the like. Generally, powders are prepared by comminuting the crystalline form to a suitable fine size and mixing with an appropriate pharmaceutical carrier such as an edible carbohydrate, as, for example, starch or mannitol. Flavorings, preservatives, dispersing agents, and coloring agents may also be present.

Capsules can be made by preparing a powder, liquid, or suspension mixture and encapsulating with gelatin or some other appropriate shell material. Glidants and lubricants such as colloidal silica, talc, magnesium stearate, calcium stearate, or solid polyethylene glycol may be added to the mixture before the encapsulation. A disintegrating or solubilizing agent such as agar-agar, calcium carbonate or sodium carbonate may also be added to improve the availability of the medicament when the capsule is ingested. Moreover, when desired or necessary, suitable binders, lubricants, disintegrating agents, and coloring agents may also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets can be formulated, for example, by preparing a powder mixture, granulating or slugging, adding a lubricant and disintegrant, and pressing into tablets. A powder mixture may be prepared by mixing the crystalline form, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture may be wet-granulated with a binder such as syrup, starch paste, acadia mucilage or solutions of cellulosic or polymeric materials, and forcing through a screen. As an alternative to granulating, the powder mixture may be run through the tablet machine and the result is imperfectly formed slugs broken into granules. The granules may be lubricated to prevent sticking to the tablet forming dies by means of the addition of stearic acid, a stearate salt, talc or mineral oil. The lubricated mixture is then compressed into tablets. The crystalline forms of the present invention may also be combined with a free flowing inert carrier and compressed into tablets directly without going through the granulating or slugging steps. A clear or opaque protective coating consisting of a sealing coat of shellac, a coating of sugar or polymeric material, and a polish coating of wax may be provided. Dyestuffs may be added to these coatings to distinguish different unit dosages.

Oral fluids such as solutions, syrups, and elixirs may be prepared in dosage unit form so that a given quantity contains a predetermined amount of the crystalline form. Syrups may be prepared, for example, by dissolving the crystalline form in a suitably flavored aqueous solution, while elixirs are prepared through the use of a non-toxic alcoholic vehicle. Suspensions may be formulated generally by dispersing the crystalline form in a non-toxic vehicle. Solubilizers and emulsifiers such as ethoxylated isostearyl alcohols and polyoxy ethylene sorbitol ethers may be added. Solubilizers that may be used according to the present invention include Cremophor EL, vitamin E, PEG, and Solutol. Preservatives and/or flavor additives such as peppermint oil, or natural sweeteners, saccharin, or other artificial sweeteners; and the like may also be added.

Where appropriate, dosage unit formulations for oral administration may be microencapsulated. The formulation may also be prepared to prolong or sustain the release as for example by coating or embedding particulate material in polymers, wax or the like.

The crystalline forms of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

The crystalline forms of the present invention may also be delivered by the use of monoclonal antibodies as individual carriers to which the crystalline form molecules are coupled.

The crystalline forms of the present invention may also be coupled with soluble polymers as targetable drug carriers. Such polymers may include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the crystalline forms may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from a patch by chemical enhancers, iontophoresis, noncavitational ultrasound, microneedles, thermal ablation, microdermabrasion, and electroporation as generally described in *Nature Biotechnology,* 26(11), 1261-1268 (2008), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The crystalline forms of the present invention may be employed alone or in combination with other therapeutic agents for the treatment of the above-mentioned conditions. For example, in frailty therapy, combination may be had with other anabolic or osteoporosis therapeutic agents. As one example, osteoporosis combination therapies according to the present invention would thus comprise the administration of at least one crystalline form of the present invention and the use of at least one other osteoporosis therapy such as, for example, Boniva® (ibandronate sodium), Fosamax® (alendronate), Actonel® (risedronate sodium), or Prolia™ (denosumab) The crystalline form(s) of the present invention and the other pharmaceutically active agent(s) may be administered together or separately and, when administered separately, administration may occur simultaneously or sequentially, in any order. The amounts of the crystalline form(s) of the present invention and the other pharmaceutically active agent(s) and the relative timings of administration will be selected in order to achieve the desired combined therapeutic effect. The administration in combination of a crystalline form of the present invention with other treatment agents may be in combination by administration concomitantly in: (1) a unitary pharmaceutical composition including both crystalline forms; or (2) separate pharmaceutical compositions each including one of the crystalline forms. Alternatively, the combination may be administered separately in a sequential manner wherein one treatment agent is administered first and the other second or vice versa. Such sequential administration may be close in time or remote in time.

Other potential therapeutic combinations include the crystalline forms of the present invention combined with other crystalline forms of the present invention, growth promoting agents, growth hormone secretagogues (e.g., ghrelin), growth hormone releasing factor and its analogs, human growth hormone and its analogs (e.g., Genotropin®, Humatrope®, Norditropin®, Nutropin®, Saizen®, Serostim®), somatomedins, alpha-adrenergic agonists, serotonin 5-$HT_D$ agonists, agents that inhibit somatostatin or its release, 5-α-reductase inhibitors, aromatase inhibitors, GnRH agonists or antagonists, parathyroid hormone, estrogen, testosterone, SERMs, progesterone receptor agonists or antagonists, and/or with other modulators of nuclear hormone receptors.

The crystalline forms of the present invention may be used in the treatment of a variety of disorders and conditions and, as such, the crystalline forms of the present invention may be used in combination with a variety of other suitable therapeutic agents useful in the treatment of those disorders or conditions. Non-limiting examples include combinations of the present invention with anti-diabetic agents, anti-osteoporosis agents, anti-obesity agents, anti-inflammatory agents, anti-anxiety agents, anti-depressants, anti-hypertensive agents, anti-platelet agents, anti-thrombotic and thrombolytic agents, cardiac glycosides, cholesterol or lipid lowering agents, mineralocorticoid receptor antagonists, phosphodiesterase inhibitors, kinase inhibitors, thyroid mimetics, anabolic agents, viral therapies, cognitive disorder therapies, sleeping disorder therapies, sexual dysfunction therapies, contraceptives, cytotoxic agents, radiation therapy, anti-proliferative agents, and anti-tumor agents. Additionally, the crystalline forms of the present invention may be combined with nutritional supplements such as amino acids, triglycerides, vitamins (including vitamin D; see, for example Hedström et al. (2002) *J Bone Joint Surg Br.* 84(4):497-503), minerals, creatine, piloic acid, carnitine, or coenzyme Q10.

In particular, the crystalline forms of the present invention are believed useful, either alone or in combination with other agents in the acceleration of wound healing and the treatment of hypogonadism, sarcopenia, osteoporosis, muscle wasting, wasting diseases, cachexia (including cachexias associated with cancer, chronic obstructive pulmonary disease (COPD), end stage renal disease (ESRD), heart failure, HIV illness, HIV treatment, and diabetes mellitus type 1 and type 2), frailty, dry eye, prostatic hyperplasia, prostate cancer, breast cancer, menopausal and andropausal vasomotor conditions, urinary incontinence, sexual dysfunction, erectile dysfunction, depression, uterine fibroid disease, endometriosis, acne, hirsutism, male contraception, impotence, and in the use as male and female hormone replacement therapy, as a stimulant of hematopoiesis, and as an anabolic agent.

ABBREVIATIONS

As used herein the symbols and conventions used in these processes, schemes and examples are consistent with those used in the contemporary scientific literature, for example, the *Journal of the American Chemical Society* or the *Journal of Biological Chemistry*. Specifically, the following abbreviations may be used in the examples and throughout the specification:

| | |
|---|---|
| g (grams); | mg (milligrams); |
| L (liters); | mL (milliliters); |
| μL (microliters); | N (normal); |
| M (molar); | mM (millimolar); |
| Hz (Hertz); | MHz (megahertz); |
| mol (moles); | mmol (millimoles); |
| rt (room temperature); | min (minute); |
| h (hour); | d (day); |
| MS (mass spec); | LCMS (liquid chromatography |
| GCMS (gas chromatography mass spec; | mass spec); |
| HPLC (high performance liquid chromatography); | |
| psi (pounds per square inch); | ESI (electrospray ionization); |
| Pd(C) palladium on carbon; | $H_2$ (hydrogen gas) |
| $NH_4Cl$ (ammonium chloride); | ee (enantiomeric excess); |
| MeCN (acetonitrile); | THF (tetrahydrofuran); |
| $Pd(PPh_3)_4$ (palladium tetrakistriphenyl phosphine); | |
| NaOH (sodium hydroxide); | $CH_2Cl_2$ (methylene chloride); |
| $CDCl_3$ (deuterated chloroform); | TFA (trifluoroacetic acid); |
| $SiO_2$ (silica); | $CD_3OD$ (deuterated methanol); |
| EtOAc (ethyl acetate); | DMSO (dimethylsulfoxide); |
| HCl (hydrochloric acid); | $Na_2SO_4$ (sodium sulfate); |
| DMF (N,N-dimethylformamide); | $CHCl_3$ (chloroform); |
| $Cs_2CO_3$ (cesium carbonate); | PhMe (toluene); |
| Et (ethyl); | Me (methyl); |
| MeOH (methanol); | EtOH (ethanol); |
| $Et_2O$ (diethyl ether); | t-Bu (tert-butyl); |
| sat'd (saturated); | $N_2$ (nitrogen); |
| $K_2CO_3$ (potassium carbonate); | $NaHCO_3$ (sodium bicarbonate); |
| NMP (N-methyl-2-pyrrolidone); | $Zn(CN)_2$ (zinc cyanide); |
| $LiBH_4$ (lithium borohydride); | DIEA (diisopropylethyl amine); |
| Oxone (potassium peroxomonosulfate); | $Et_3N$ (triethylamine); |
| $Na_2S_2O_3$ (sodium thiosulphate); | LDA (lithium diisopropylamide); |
| PTFE (polytetrafluoroethylene); | DIPA (diisopropylamine); |
| hex (hexanes); | KOtBu (potassium t-butoxide); |
| $NaCNBH_3$ (sodium cyanoborohydride); | semiprep (semipreparative); |
| $Pd(PPh_3)_2Cl_2$ (bis(triphenylphosphine)palladiumchloride); | |
| anhyd (anhydrous); | CuI (copper iodode); |
| dppf (1,1'-bis(diphenylphosphino)ferrocene); | |
| $Pd_2(dba)_3$ (tris(dibenzylideneacetone)dipalladium(0); | |
| PMHS (polymethylhydrosiloxane); | DMAC (dimethyacetamide); |
| Aq (aqueous); | MsCl (mesyl chloride); |
| n-BuLi (n-butyllithium); | TBAF (tetra-n-butylammonium |
| MTBE (methyl t-butyl ether); | fluoride) |
| | TsOH (tosic acid); |
| | $Boc_2O$ (di-t-butyl dicarbonate). |

Unless otherwise indicated, all temperatures are expressed in ° C. (degrees Centigrade). All reactions conducted under an inert atmosphere at room temperature unless otherwise noted. Reagents employed without synthetic details are commercially available or made according to literature procedures.

X-ray powder diffraction (XRPD) data as shown in FIGS. 1 and 2 were acquired on a PANalytical X'Pert Pro powder diffractometer, model PW3040 Pro, using an X'Celerator detector. The acquisition conditions were: radiation: Cu Kα, generator tension: 45 kV, generator current: 40 mA; step size: 0.0084° 2θ; continuous scan; incident beam optics: mirror optics—Cu W/Si (Focusing MPD), ½ degree fixed divergence slit, 0.02 radian soller slits; diffracted beam optics: programmable anti-scatter slit assembly (X'celerator module) set to fixed ½ degree anti-scatter slit, 0.02 radian soller slits, measurement temperature: 20-25° C. The sample was prepared by packing sample in a 1.0 mm capillary. Peak positions were obtained using PANalytical X'Pert Highscore Plus software. The margin of error is approximately ±0.1° 2θ for each of the peak assignments.

$^{13}$C and $^{19}$F solid state NMR data as shown in FIGS. 3-6 were acquired using a Bruker Avance 500 triple-resonance spectrometer operating at a $^1$H frequency of 499.98 MHz. The $^{13}$C SSNMR spectra shown were obtained using a cross-polarization pulse sequence with a Bruker 4-mm triple resonance magic-angle spinning probe at a rotor frequency of 8 kHz. A linear power ramp from 75 to 90 kHz was used on the $^1$H channel to enhance cross-polarization efficiency. Spinning sidebands were eliminated by a five-pulse total sideband suppression pulse sequence. $^1$H decoupling was obtained using the Spinal-64 sequence. The $^{19}$F SSNMR spectra shown were obtained using a cross-polarization pulse sequence with a Bruker 4-mm triple resonance magic-angle probe at a rotor frequency of 12.5 kHz. The sample temperature was approximately 0° C. Characteristic $^{13}$C and $^{19}$F NMR peak positions are reported relative to tetramethylsilane at 0 ppm (parts per million) and are quoted to a precision of +/−0.2 ppm, because of instrumental variability and calibration.

EXAMPLES

Example 1

Synthesis of (R)-1-(1-(methylsulfonyl)propan-2-yl)-4-(trifluoromethyl)-1H-indole-5-carbonitrile (R)-1-(1-(methylsulfonyl)propan-2-yl)-4-(trifluoromethyl)-1H-indole-5-carbonitrile Method 1

A. (R)-1-(Methylthio)propan-2-amine

Step 1

To a solution of commercially available (R)-2-aminopropan-1-ol (5 g, 66.6 mmol) in MeCN (20 mL), in an ice bath, is added very slowly, dropwise, chlorosulfonic acid (4.46 mL, 66.6 mmol) (very exothermic). The reaction mixture is kept in the cold bath for ~10 min, and then at rt for ~30 min. After stirring for another ~10 minutes, the solids are collected by filtration, washed sequentially with MeCN (40 mL) and hexanes (100 mL), and dried by air suction for ~40 min. to produce the intermediate ((R)-2-aminopropyl hydrogen sulfate.

Step 2

To a solution of sodium thiomethoxide (5.60 g, 80 mmol) in water (20 mL) is added solid NaOH (2.66 g, 66.6 mmol) in portions over ~10 min. Then the intermediate from step 1 is added as a solid over ~5 min. The mixture is then heated at 90° C. for ~10 h. The reaction mixture is biphasic. Upon cooling, MTBE (20 mL) is added, and the organic phase (brownish color) is separated. The aqueous phase is extracted with MTBE (2×20 mL). The original organic phase is washed with 1N NaOH (15 mL). The basic aqueous phase is re-extracted with MTBE (2×20 mL). All the ether phases are combined, dried over Na$_2$SO$_4$, filtered, and concentrated (carefully, since the product is volatile) to afford the crude product as a light yellow oil.

Method 2

(R)-1-(methylthio)propan-2-amine hydrochloride

A. (R)-2-((tert-Butoxycarbonyl)amino)propyl methanesulfonate

Step 1

Commercially available (R)-2-aminopropan-1-ol (135 g, 1797 mmol) is dissolved in MeOH 1350 mL). The solution is cooled to 5° C. with an icebath, then Boc$_2$O (392 g, 1797 mmol) is added as a solution in MeOH (1000 mL). The reaction temperature is kept below 10° C. After the addition, the cooling bath is removed, and the mixture is stirred for 3 h. The MeOH is removed under vacuum (rotavap bath: 50° C.). This material is used as is for the next step.

Step 2

The residue is dissolved in CH$_2$Cl$_2$ (1200 mL) and NEt$_3$ (378 mL, 2717 mmol) is added, then the mixture is cooled on an ice bath. Next, MsCl (166.5 mL, 2152 mmol) is added over ~2 h, while keeping the reaction temperature below 15° C. The mixture is stirred in an icebath for 1 h then the bath was removed. The mixture is stirred for 3 d, then washed with a 10% NaOH solution (500 mL 3×), then with water. The organic phase is dried with MgSO$_4$, filtered, then stripped off (rota, 50° C. waterbath. The impure residue is dissolved in a mix of 500 mL EtOAc (500 mL) and MTBE (500 mL) and then extracted with water to remove all water-soluble salts. The organic phase is dried with MgSO$_4$, filtered, then stripped off to afford a white solid residue.

B. (R)-tert-Butyl (1-(methylthio)propan-2-yl)carbamate

NaSMe (30 g, 428 mmol) is stirred with DMF (200 mL) to afford a suspension. Next, (R)-2-((tertbutoxycarbonyl) amino)propyl methanesulfonate (97 g, 383 mmol) is added portionwise while the temperature is kept below 45° C. (exothermic). After the addition, the mixture is stirred for 2 h, then toluene (100 mL) is added. The mixture is washed with water (500 mL, 4×), then dried with MgSO$_4$, and filtered. The filtrate is stripped off (rotavap) to a pale yellow oil.

C. (R)-1-(Methylthio)propan-2-amine hydrochloride

Acetyl chloride (150 mL,) is added to a stirred solution of MeOH (600 mL) cooled with an icebath. The mixture is stirred for 30 min in an icebath, then added to (R)-tert-butyl (1-(methylthio)propan-2-yl)carbamate (78 g, 380 mmol). The mixture is stirred at rt for 2 h, (CO$_2$, (CH$_3$)$_2$C=CH$_2$ evolution) and then stripped off to a white solid.

D. 4-Fluoro-3-iodo-2-(trifluoromethyl)benzonitrile

To a freshly prepared solution of LDA (119 mmol) in anhyd THF (250 mL) at −45° C. is added a solution of commercially available 4-fluoro-2-(trifluoromethyl)benzonitrile (21.5 g, 114 mmol) in THF (30 mL), dropwise at a rate such that the internal temperature remained <−40° C. (became dark brown during addition). The mixture is stirred 30 min at −45° C., cooled to −70° C. and iodine (31.7 g, 125 mmol) is added in one portion (−70° C.→−52° C.). The mixture is stirred for 1 h, removed from the cooling bath and quenched by addition of 10% Na$_2$S$_2$O$_3$ (ca. 250 mL) and 1N HCl (ca. 125 mL). The mixture is extracted with EtOAc (×3). Combined organics are washed (water, brine), dried over Na$_2$SO$_4$ and concentrated in vacuo. The residue is purified by low pressure liquid chromatography (silica gel, EtOAc hexanes, gradient elution) followed by recrystallization from heptane (30 mL), twice, affording 4-fluoro-3-iodo-2-(trifluoromethyl)benzonitrile (15.79 g, 50.1 mmol, 44.1% yield) as a pale yellow solid.

E. 4-Fluoro-2-(trifluoromethyl)-3-((trimethylsilyl) ethynyl)benzonitrile

A 20 mL vial is charged with 4-fluoro-3-iodo-2-(trifluoromethyl)benzonitrile, (0.315 g, 1.00 mmol), Pd(PPh$_3$)$_2$Cl$_2$ (0.014 g, 0.020 mmol) and CuI (0.0076 g, 0.040 mmol), and sealed with a rubber septum. Anhyd PhMe (5 mL) and DIPA (0.210 mL, 1.500 mmol) are added via syringe and the mixture is degassed 10 min by sparging with N$_2$ while immersed in an ultrasonic bath. Ethynyltrimethylsilane (0.155 mL, 1.100 mmol) is added dropwise via syringe and the septum is replaced by a PTFE-faced crimp top. The mixture is stirred in a heating block at 60° C. Upon cooling the mixture is diluted with EtOAc and filtered through Celite. The filtrate is washed (satd NH$_4$Cl, water, brine), dried over Na$_2$SO$_4$ and concentrated in vacuo. The residue is purified by low pressure liquid chromatography (silica gel, EtOAc hexanes, gradient elution) affording 4-fluoro-2-(trifluoromethyl)-3-((trimethylsilyl)ethynyl)benzonitrile.

F. (R)-1-(1-(methylthio)propan-2-yl)-4-(trifluoromethyl)-1H-indole-5-carbonitrile A mixture of 4-fluoro-2-(trifluoromethyl)-3-((trimethylsilyl)ethynyl)benzonitrile (1.16 g, 4.07 mmol), (R)-1-(methylthio)propan-2-amine (0.599 g, 5.69 mmol) and DIEA (1.42 mL, 8.13 mmol) in DMSO (7 mL) is heated (sealed tube) at 100° C. for 50 min. Upon cooling, the reaction mixture is diluted with EtOAc (50 mL) and washed with water (30 mL). The organic phase is washed with water and brine, dried over $Na_2SO_4$, filtered and concentrated to give the intermediate aniline. This intermediate is dissolved in NMP (7 mL), treated with KOtBu (1 M in THF) (5.69 mL, 5.60 mmol) and heated at 50° C. The reaction is monitored by LCMS, and deemed complete after 40 min. Upon cooling, the reaction mixture is diluted with EtOAc (40 mL) and washed with water (30 mL). The organic phase is washed with more water and brine, dried over $Na_2SO_4$, filtered and concentrated. The residue is chromatographed over silica gel using a 5-40% EtOAc-hexane gradient to give the thioether intermediate:

G. (R)-1-(1-(methylsulfonyl)propan-2-yl)-4-(trifluoromethyl)-1H-indole-5-carbonitrile To an ice-cold solution of (R)-1-(1-(methylthio)propan-2-yl)-4-(trifluoromethyl)-1H-indole-5-carbonitrile (0.560 g, 1.88 mmol) in MeOH (10 mL) is added a solution of Oxone (4.04 g, 6.57 mmol) in water (10 mL). After 50 min, the reaction mixture is diluted with water (30 mL) and extracted with EtOAc (50 mL). The organic phase is washed with brine, dried over $Na_2SO_4$, filtered and concentrated. The residue is chromatographed over silica gel using 100% $CH_2Cl_2$ to give (R)-1-(1-(methylsulfonyl)propan-2-yl)-4-(trifluoromethyl)-1H-indole-5-carbonitrile as a white foam that is crystallized from $CH_2Cl_2$/hexanes to afford a white solid.

Example 2

Preparation of crystalline form 1 of (R)-1-(1-(methylsulfonyl)propan-2-yl)-4-(trifluoromethyl)indoline-5-carbonitrile

(R)-1-(1-(methylsulfonyl)propan-2-yl)-4-(trifluoromethyl)indoline-5-carbonitrile (1.74 kg, 1 wt) was dissolved in ethyl acetate (12.0 Kg, 6.9 wt) at 20-30° C. The solution was transferred into a clean reaction vessel via an in-line cartridge filter. The solution was concentrated to ~3.0-5.0 volumes under reduced pressure, keeping the temperature below 50° C. The solution was cooled to 20-30° C., and n-heptane (23.0 Kg, 13.2 wt) was added slowly over ~1 hour. The solution was stirred 1-2 hrs at 20-30° C., heated to 50-55° C. for 2-3 hours, cooled back to 20-30° C. and stirred for 1-2 hours. The slurry was sampled and analyzed by XRPD. The solid was collected by filtration, washed with n-heptane (1.4 Kg, 0.8 wt), and dried in vacuo at 40-50° C. to provide crystalline (R)-1-(1-(methylsulfonyl)propan-2-yl)-4-(trifluoromethyl)indoline-5-carbonitrile (1.54 Kg, Form 1; 88.5% yield, 99.5% purity) as a slightly colored solid.

Example 3

Preparation of crystalline form 2 of (R)-1-(1-(methylsulfonyl)propan-2-yl)-4-(trifluoromethyl)indoline-5-carbonitrile Crude (R)-1-(1-(methylsulfonyl)propan-2-yl)-4-(trifluoromethyl)indoline-5-carbonitrile (1.54 g [theoretical], 1 wt) was dissolved in dichloromethane (5 mL, 3.25 vol) and loaded onto a 12-g ISCO column ($SiO_2$). The column was eluted with DCM (~500 mL, 325 vol) and the product-containing fractions were combined and concentrated in vacuo. The resulting residue was triturated in n-heptane. The solid was collected by filtration, air-dried, and placed under high vacuum for 3 h to provide GSK2881078A (1.009 g, Form 2; 65.1% yield, 100% AUC HPLC-UV) as a white solid.

That which is claimed:
1. A crystalline form of:

that is characterized by an X-ray powder diffraction (XRPD) pattern that has the representative peaks:

| Position [°2Theta] | d-spacing [Å] |
|---|---|
| 7.4 ± 0.1 | 11.9 |
| 12.7 ± 0.1 | 7.0 |
| 17.5 ± 0.1 | 5.1 |
| 19.5 ± 0.1 | 4.6 |
| 21.9 ± 0.1 | 4.1 |
| 22.5 ± 0.1 | 3.9 |
| 23.9 ± 0.1 | 3.7 |
| 26.5 ± 0.1 | 3.4. |

2. The crystalline form of claim 1 that is further characterized by an XRPD pattern substantially in accordance with FIG. 2.
3. The crystalline form of claim 1 that is further characterized by an $^{19}F$ SSNMR spectrum comprising isotropic chemical shifts at −55.5±0.2 and −56.3±0.2 ppm, wherein the $^{19}F$ SSNMR spectrum is obtained on a spectrometer operating at a frequency of 470.40 MHz for $^{19}F$ observation using a cross-polarization pulse sequence with a Bruker 4-mm triple resonance magic-angle spinning probe at a rotor frequency of 12.5 kHz.
4. The crystalline form of claim 1 that is further characterized by an $^{19}F$ SSNMR spectrum substantially in accordance with FIG. 6.

5. The crystalline form of claim 1 that is further characterized by an $^{13}$C SSNMR (solid state nuclear magnetic resonance) spectrum comprising isotropic chemical shifts at 138.4±0.2, 127.4±0.2, 125.5±0.2, 124.3±0.2, 123.3±0.2 116.5±0.2, 114.1±0.2, 104.7±0.2, 97.4±0.2, 61.8±0.2, 60.9±0.2, 59.2±0.2, 48.2±0.2, 47.6±0.2, 46.3±0.2, 44.4±0.2, 42.3±0.2 , and 26.1±0.2 ppm, wherein the $^{13}$C SSNMR spectrum is obtained on a spectrometer operating at a frequency of 125.73 MHz for $^{13}$C observation using a cross-polarization pulse sequence with a Bruker 4-mm triple resonance magic-angle spinning probe at a rotor frequency of 8kHz.

6. The crystalline form of claim 1 that is further characterized by an $^{13}$C SSNMR spectrum substantially in accordance with FIG. 5.

7. A method of treating a disorder selected from muscle wasting associated with chronic obstructive pulmonary disease (COPD), muscle wasting associated with chronic kidney disease (CKD), muscle wasting associated with chronic heart failure (CHF), and urinary incontinence, wherein said method comprises administering a compound according to claim 1 to a human subject.

8. A method of accelerating hip fracture repair and healing, wherein said method comprises administering a compound according to claim 1 to a human subject.

* * * * *